United States Patent [19]

Hjort

[11] 4,275,743

[45] Jun. 30, 1981

[54] MEASURING DEVICE FOR MEASURING THE BIOELECTRICAL ACTIVITY OF THE CENTRAL NERVOUS SYSTEM

[75] Inventor: Bo Hjort, Sollentuna, Sweden

[73] Assignee: Siemens Aktiengesellschaft, Berlin & Munich, Fed. Rep. of Germany

[21] Appl. No.: 57,127

[22] Filed: Jul. 11, 1979

[30] Foreign Application Priority Data

Jul. 17, 1978 [DE] Fed. Rep. of Germany ....... 2831412

[51] Int. Cl.³ .............................................. A61B 5/04
[52] U.S. Cl. ................................... 128/731; 128/644
[58] Field of Search ............................... 128/639–644, 128/710–712, 731–734

[56] References Cited

U.S. PATENT DOCUMENTS

| 3,367,323 | 2/1968 | Schuler | 128/643 X |
| 4,084,583 | 4/1978 | Hjort | 128/731 |

OTHER PUBLICATIONS

"Handbook of EEG", Elsevier Scientific Publishing Co., Amsterdam, 1974, vol. 3, Part 3, pp. 3C-22–3C-57.

Primary Examiner—Lee S. Cohen
Attorney, Agent, or Firm—Hill, Van Santen, Steadman, Chiara & Simpson

[57] ABSTRACT

In an exemplary embodiment, a plurality of electrodes to be applied to the patient are employed and potential differences between the electrodes and a reference potential derived from the electrode potentials are formed. Weighting resistors are interposed which weight the potential differences, and the weighted values are combined in such a manner that the potential components proceeding from a specific point under the electrode system and especially from a point below the scalp are comprehended according to their magnitude while signal components proceeding from other points are suppressed.

4 Claims, 5 Drawing Figures

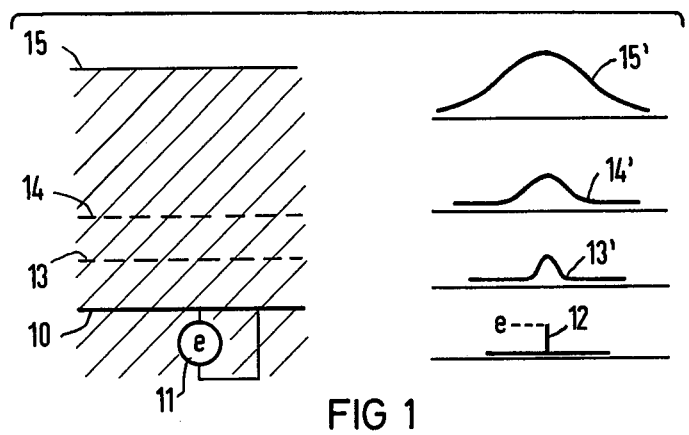
FIG 1
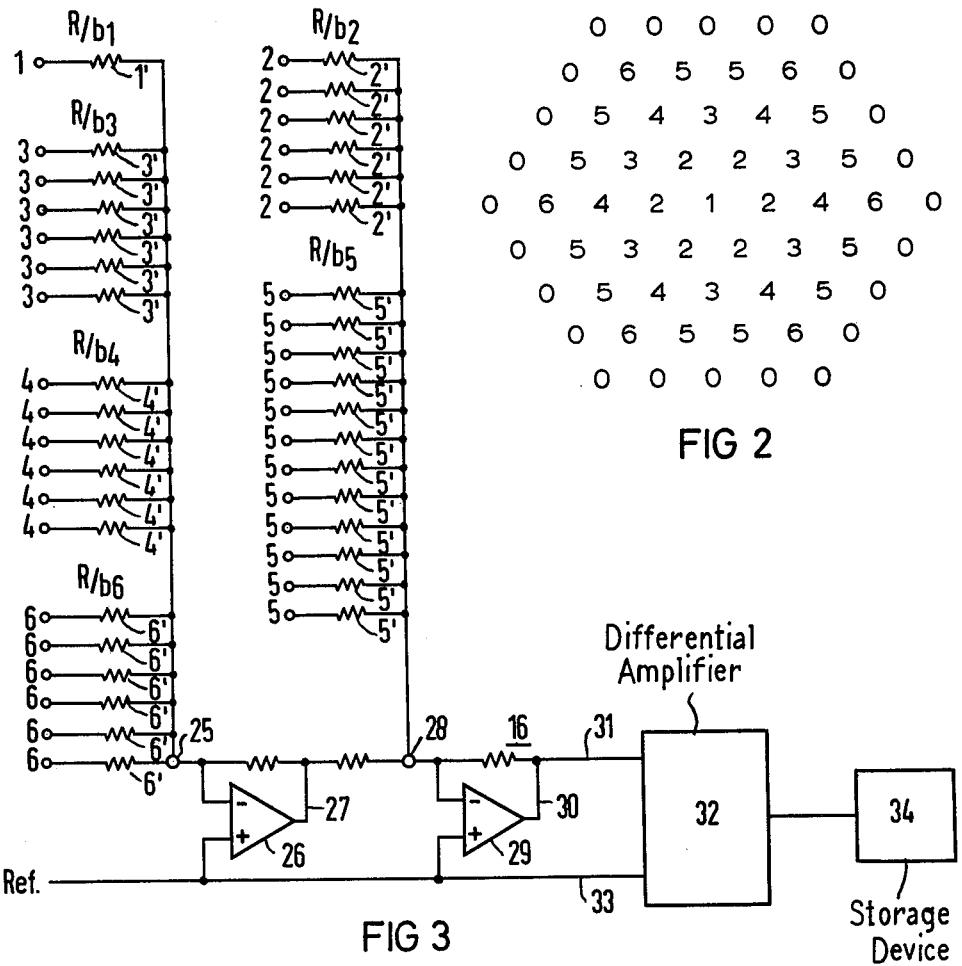
FIG 2
FIG 3

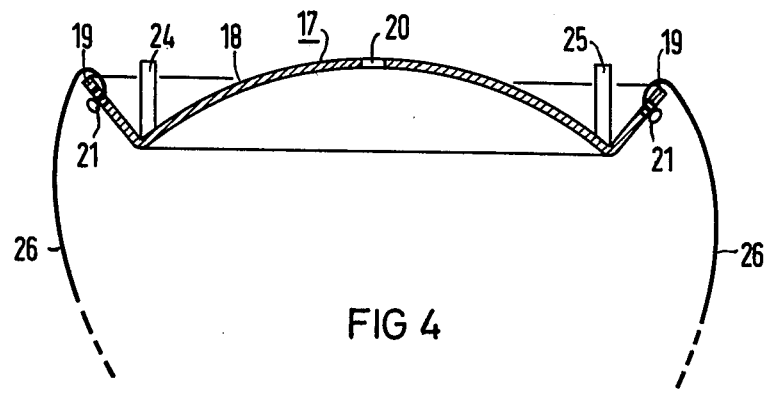
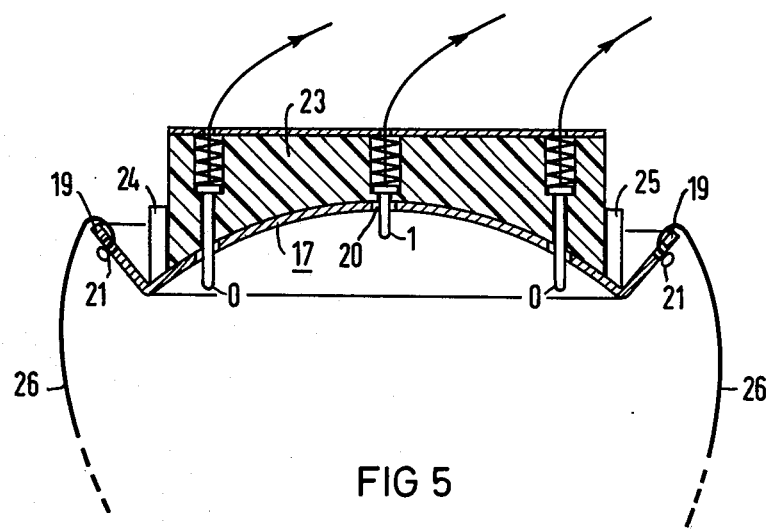

MEASURING DEVICE FOR MEASURING THE BIOELECTRICAL ACTIVITY OF THE CENTRAL NERVOUS SYSTEM

BACKGROUND OF THE INVENTION

The invention relates to a measuring device for measuring the bioelectrical activity of the central nervous system in which a plurality of electrodes which can be placed on the patient are employed and in which the potential differences between the electrodes and a reference potential derived from the electrode potentials are formed.

In known measuring devices of this type, the measurement ensues either by means of a plurality of electrodes arranged according to an international standardization on the scalp (electroencephalograph EEG) or by means of a plurality of electrodes which are applied to the exposed cerebral cortex or to the meninx (electrocortigraphy, ECoG). The electrical activity of the nerve cells and of the surrounding medium is comprehended under the electrodes as corresponding potential changes. In both cases, amplifiers and registering devices are post-connected to the electrodes.

The known measuring processes which are carried out with such measuring devices are divided into bipolar and unipolar measuring processes as they are illustrated and described in the "Handbook of Electroencephalography", Elsevier Scientific Publishing Company, Amsterdam, 1974, Volume 3, Part 3, particularly in FIGS. 10 and 13 with the appertaining description. In a bipolar measuring process, differential voltages are conducted to the amplifier inputs which are realized in pairs between the electrodes. Thereby, each measured voltage is the difference between two electrode potentials. A selective covering of each localized electrode potential change does not ensue. Accordingly, it is difficult to precisely localize the cerebral bioelectrical activity. In a unipolar measuring process, differential voltages are comprehended between a plurality of electrodes and a respective reference point provided in common for these electrodes. This reference point can be a physical electrode or, for example, the midpoint of a resistance star which is connected to all electrodes with the same amount of resistance, possibly with the exception of those electrodes whose signals could falsify the measuring result because, for example, they are caused by means of muscle activity. In the majority of electrodes employed, it has up to now resulted by necessity that not all reference-forming electrodes are arranged neighboring the signal electrode, but that, rather, they were distributed over the entire scalp of the patient. For this reason, it was not possible to comprehend a potential which was a measure for the bioelectrical activity in the direct area of the signal electrode. On the contrary, only potential differences were measured which allowed of no precise conclusions concerning the location of the measured bioelectrical activity.

In the German AS No. 25 18269 (corresponds to the U.S. Pat. No. 4,084,583), a measuring process is described in which only such electrodes are used as the auxiliary electrodes for a signal electrode which neighbor the signal electrode. In the registration of a cerebral electrical activity with the assistance of surface electrodes on the scalp, however, a spreading effect is present in contrast to the registration of potential distributions in tissues which lie deeper, for example, on the cortex. There is a desire, however, to know the potentials prevailing on the cortex.

SUMMARY OF THE INVENTION

Accordingly, the object of the invention is to create a measuring device of the type initially cited in which the bioelectrical activity of the central nervous system can be determined at a location which lies as close as possible to the cortex.

This object is inventively achieved in that means are present which weight the potential differences with a weighting factor in such manner and subsequently sum them so that the potential components proceeding from a specific point beneath the electrode system are comprehended according to their magnitude, and signal components proceeding from other points are suppressed. Based on the fact that a point potential below the scalp surface on or near the cortex can be determined from the potential field of the scalp surface which has a distribution similar to a gauss bell curve for a point potential on the cortex, it is possible to determine the potential distribution in a plane close to the cortex even given the employment of surface electrodes.

The weighting factors are selected in such manner that those potential components which proceed from the interesting locations are comprehended, and the potential components proceeding from the other locations are suppressed. By means of summing the weighted signals, one then receives a signal which very precisely reproduces the potential at the interesting location on the cortex.

Further details of the invention derive from the subclaims. In the following, the invention is described in greater detail on the basis of an exemplary embodiment illustrated on the accompanying sheets of drawings; and other objects, features and advantages will be apparent from this detailed disclosure and from the appended claims.

BRIEF DESCRIPTION OF THE DRAWINGS

FIG. 1 is a schematic illustration of the spread of the cerebral electrical activity from a point of the cortex to the scalp surface;

FIG. 2 shows diagrammatically the electrode configuration for a measuring device according to the invention;

FIG. 3 shows a circuit arrangement of a measuring device according to the invention;

FIG. 4 shows a fastening arrangement for an electrode mount for a measuring device according to the invention; and FIG. 5 shows an electrode mount for a measuring device according to the invention.

DETAILED DESCRIPTION

FIG. 1 shows a schematic illustration of a cross section through the tissue of a scalp from the scalp surface to the cortex. The cerebral electrical activity changes on the path from the cortex to the scalp surface in that a spreading occurs in the tissue lying between, so that each potential component of the cortex occurs at the scalp surface with a potential distribution of a specific width. The potential at each point in the potential field of the scalp surface is therefore composed of various potential components which come from various locations of the cortex. A voltage source 11 is illustrated on the cortex 10 which is meant to represent the cerebral electrical activity at one point. The magnitude of the activity at the point is designated with 12. The spread of the potential at the Niveau 13 is represented by means of the curve 13' which is approximately bell shaped. At the Niveau 14, the spread of this potential is even greater, as the curve 14' shows. The potential spread is greatest at the scalp surface 15 as the bell-shaped curve 15' shows.

FIG. 2 shows sixty-one (61) electrodes placed on the scalp of a patient in a specific geometrical configuration. Here, the magnitude of the cerebral electrical activity at the cortex is to be measured precisely below the signal electrode 1. Reference electrodes have been designated with 0 and 2 through 6, whereby the electrodes 0 are the boundary electrodes. The interval between the electrodes is approximately 10 mm.

The signals which are obtained between these electrodes 0, 1, 2 through 6 and a reference point are weighted and summed. The weighting and summation ensues in such manner that the effect under the point in question is suppressed as to components occurring at the surface with a potential spread which is not centered under the interesting point or which occur with a potential spread which is larger than the spread of a point potential in a plane in the proximity of the cortex at the surface of the scalp.

The weighting coefficients are selected in such manner that the measuring plane lies as close as possible to the cortex in order to achieve the greatest possible precision in the registration of individual potential components.

The weighting coefficients are selected for a measuring plane at a depth which corresponds to a gauss spread of a point potential with a width which is equal to 1.6 times the electrode interval.

The calculation of a weighting coefficient can be carried out with the assistance of a matrix algebra and is a known process in image processing technology (Harry C. Andrews, Computer Techniques in Image Processing, Academic Press, 1970, New York).

When the weighting coefficient is designated with b and the electrodes with 1 through 6, the weighting coefficients are as follows:

$b_1 = +0.38$; $b_2 = 0.72$ (for each of six electrodes 2); $b_3 = +0.51$ (for each of six electrodes 3); $b_4 = +0.02$ (for each of six electrodes 4); $b_5 = -0.27$ (for each of twelve electrodes 5); $b_6 = +0.06$ (for each of six electrodes 6).

The potential differences between the potentials of the thirty-seven (37) electrodes 1 through 6 multiplied by the corresponding weighting coefficients, and a reference potential (Ref.) which is the mean potential of all sixty-one (61) electrode potentials, are processed by means of a circuit arrangement according to FIG. 3. It is shown in this figure that resistances 1' through 6' whose sizes correspond inversely to the weighting factors $b_1$ through $b_6$ lie between the electrodes 1 through 6 and a summation circuit 16.

A signal corresponding to the sum of the weighted signals of the electrodes 1, 3, 4, and 6 is obtained at the summation point 25 and is supplied to the negative input of an operational amplifier 26. The reference potential (Ref.) is supplied to the positive input of this operational amplifier 26. A potential which corresponds to the summation current at point 25 is obtained at the output 27 of the operational amplifier 26. A current corresponding to the sum of the weighted signals of the electrodes 2 and 5 is obtained at the summation point 28. The current at point 28 is subracted from the current at point 25 and the differential current is supplied to the negative input of a further operational amplifier 29. The reference potential (Ref.) likewise lies at the positive input of this operational amplifier 29. A signal thus lies at the output 30 of the amplifier 29 which is obtained from the electrode potentials in the manner described in conjunction with FIG. 2. This final potential is now supplied to the one input 31 of a differential amplifier 32. At the same time, the reference potential is supplied to a second input 33 of the differential amplifier 32. The difference between these signals is supplied to a storage or recording device 34. The output signal of the differential amplifier 32 corresponds to the point potential at the cortex directly below the electrode 1.

FIG. 4 shows a fastening arrangement 17 with a concaveshaped plate 18 with a raised edge 19. The plate 18 has holes which correspond to the electrode configuration according to FIG. 2. The center hole 20, corresponding to the position of the electrode 1, serves as the point of reference, i.e., that the operating personnel apply the fastening arrangement 17 to the scalp of the patient in such manner that the point of reference lies on the point to be investigated. The fastening arrangement 17 can be secured to the scalp of the patient by means of a strap 26 which is arranged on the raised edge 19 at the fastening locations 21 and can be applied under the chin of the patient.

FIG. 5 shows that an electrode mount 23 of insulating material can be placed on the fastening arrangement 17 and be aligned by means of two nipples 24, 25. The electrodes 1 through 6 are spring-seated in the mount 23 approximately perpendicular to the application surface, of which only three (3) electrodes are illustrated here. The electrodes, whose ends can be pointed or round, are approximately 2 mm in diameter. The electrodes 0, 1 through 6 are connected with a differential amplifier according to FIG. 3 via lines.

The measuring device with a circuit arrangement for the weighting and summation of the electrode signal is, according to the invention, a device for the focusing of scalp potential registrations on a measuring plane lying below the scalp and thus renders possible an improved diagnosis of localized phenomena in the electrical activity of the brain.

It will be apparent that many modifications and variations may be effected without departing from the scope of the novel concepts and teachings of the present invention.

I claim as my invention:

1. Measuring apparatus for measuring bioelectrical activity of the central nervous system, said apparatus comprising a multiplicity of electrodes (0, 1 through 6) arranged in an area array for providing an extensive covering pattern for an exterior application surface of a patient, said area array having a midpoint at one of the electrodes (1) for alignment with respect to an interior point beneath the patient exterior application surface whose potential is to be measured, the electrodes (0, 2 through 6) being arranged at a multiplicity of different distances from the midpoint of the area array such that the electrodes of the area array exhibit a multiplicity of different distances from such interior point during a measurement operation, and means (1'-6', 16) coupled with the respective electrodes (0, 1 through 6) and responsive to the potentials of the respective electrodes during a measurement operation to transmit weighted potentials in accordance with the potentials of the respective electrodes but with a relative weighting thereof in accordance with a multiplicity of respective different weighting factors corresponding to the spreading out of a hypothetical potential emanating from such interior point via respective paths penetrating the tissue layers between such interior point and the respective electrodes at the patient exterior application surface, and sum the weighted potentials for the respective electrodes such that a sum signal is produced essentially exclusively representing the magnitude of the potential at the interior point.

2. A measuring device according to claim 1, characterized in that said means comprises a summation circuit (16), and resistances (1' through 6') whose resistance values correspond to the weighting factors, the resistances being connected between the electrodes (1 through 6) and the summation circuit (16) for the purpose of weighting.

3. A measuring device according to claim 1, characterized in that a mount (18, 23) has the electrodes (0, 1 through 6) secured in a predetermined geometrical arrangement, said mount (18, 23) having means accommodating its application to the head of a patient.

4. A measuring device according to claim 3, characterized in that the electrodes (0, 1 through 6) are spring-seated in the mount (18, 23) so as to be approximately perpendicular to the application surface.

* * * * *